(12) United States Patent
Nakamura et al.

(10) Patent No.: US 10,376,601 B2
(45) Date of Patent: Aug. 13, 2019

(54) IN-VIVO INTRAVASCULAR BLOOD REPLACING LIQUID, IN-VIVO INTRAVASCULAR BLOOD REPLACING LIQUID FORMULATION, AND PREFILLED SYRINGE

(71) Applicant: TERUMO KABUSHIKI KAISHA, Shibuya-ku, Tokyo (JP)

(72) Inventors: Koji Nakamura, Hadano (JP); Isao Mori, Chofu (JP); Masanori Tokida, Fujinomiya (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 0 days.

(21) Appl. No.: 15/277,405

(22) Filed: Sep. 27, 2016

(65) Prior Publication Data

US 2017/0014535 A1    Jan. 19, 2017

Related U.S. Application Data

(63) Continuation of application No. PCT/JP2014/080001, filed on Nov. 12, 2014.

(30) Foreign Application Priority Data

Mar. 28, 2014  (JP) ................. 2014-070571

(51) Int. Cl.
| | |
|---|---|
| *A61K 49/22* | (2006.01) |
| *A61B 1/00* | (2006.01) |
| *A61K 49/04* | (2006.01) |
| *A61B 8/12* | (2006.01) |
| *A61B 8/08* | (2006.01) |
| *A61M 5/178* | (2006.01) |
| *A61M 25/00* | (2006.01) |
| *A61B 8/00* | (2006.01) |
| *A61M 5/00* | (2006.01) |
| *A61M 5/31* | (2006.01) |

(52) U.S. Cl.
CPC ........ *A61K 49/226* (2013.01); *A61B 1/00165* (2013.01); *A61B 8/12* (2013.01); *A61B 8/445* (2013.01); *A61B 8/481* (2013.01); *A61K 49/0409* (2013.01); *A61M 5/178* (2013.01); *A61M 25/0097* (2013.01); *A61M 5/007* (2013.01); *A61M 2005/3104* (2013.01); *A61M 2025/0059* (2013.01)

(58) Field of Classification Search
CPC .................................. A61K 49/0409
See application file for complete search history.

(56) References Cited

U.S. PATENT DOCUMENTS

| | | | |
|---|---|---|---|
| 2009/0162438 A1 | 6/2009 | Fuller et al. | |
| 2010/0076320 A1 | 3/2010 | Petersen et al. | |
| 2010/0143498 A1* | 6/2010 | Shigeta ............... | A61K 9/0019 424/643 |
| 2010/0317581 A1 | 12/2010 | Garcia Rubio et al. | |
| 2011/0245683 A1 | 10/2011 | Onimura | |
| 2014/0205542 A1 | 7/2014 | Vogel et al. | |

FOREIGN PATENT DOCUMENTS

| | | | | |
|---|---|---|---|---|
| JP | 2010-512230 A | 4/2010 | | |
| JP | 2011-507635 A | 3/2011 | | |
| JP | 2011-206375 A | 10/2011 | | |
| JP | 2012-529510 A | 11/2012 | | |
| JP | 2013-500142 A | 1/2013 | | |
| JP | 2015-10065 A | 1/2015 | | |
| WO | 2010/144265 A2 | 12/2010 | | |
| WO | WO 2012/102210 A1 | 8/2012 | | |
| WO | WO2012/174478 | * 12/2012 | ............. | A61K 38/28 |

OTHER PUBLICATIONS

Baker et al. Arthritis and Rheumatism, 1989, 32(4):461-467.*
Mitchell et al. J Thorac CardiovasC Surg., 1994, 107:1481-1488.*
Bhatoe, Indian J of Neurothrauma, 2005, 2(1):1-2.*
Espigares et al. J of Hospital Infection, 2003, 55:137-140.*
Notification of Transmittal of Translation of the International Preliminary Report on Patentability (Form PCT/IB/338 and Form PCT/IB/373) and Written Opinion of the International Searching Authority (Form PCT/ISA/237) dated Oct. 13, 2016, by the International Bureau of WIPO in corresponding International Patent Application No. PCT/JP2014/080001. (9 pgs).
International Search Report (PCT/ISA/210) dated Feb. 17, 2015, by the Japanese Patent Office as the International Searching Authority for International Application No. PCT/JP2014/080001.
Office Action dated Aug. 7, 2018 in corresponding Japanese Patent Application No. 2016-509899, and an English translation thereof.
Office Action dated Apr. 25, 2017 in corresponding Japanese Patent Application No. 2013-136994, and an English translation thereof.
"New Pharmaceutics Outline" (the 3rd edition of revision), Nankodo Co., Ltd., Apr. 10, 1987, p. 414.

* cited by examiner

*Primary Examiner* — Bin Shen
(74) *Attorney, Agent, or Firm* — Buchanan Ingersoll & Rooney PC

(57) ABSTRACT

An in-vivo intravascular blood replacing liquid of the present invention is injected into a blood vessel to replace blood at an intravascular portion to be inspected therewith in making an in-vivo intravascular inspection. The blood replacing liquid comprises an aqueous medium unharmful for a living body and a gelling property imparting substance, unharmful for the living body, which is added to the aqueous medium to impart a gelling property to the blood replacing liquid. The blood replacing liquid has a viscosity of not more than 3 mPa·s when the blood replacing liquid is injected into the blood vessel.

13 Claims, 9 Drawing Sheets

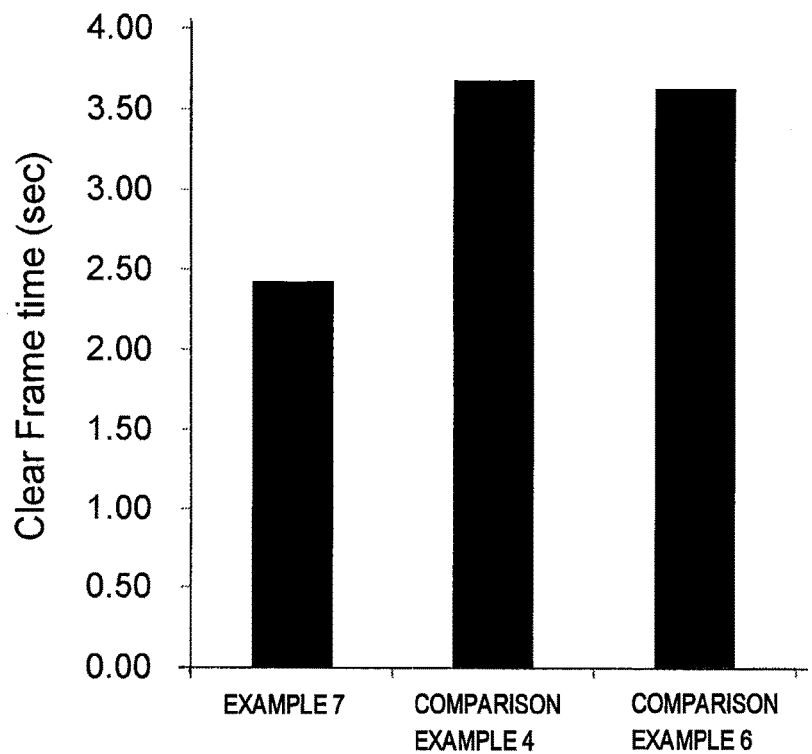
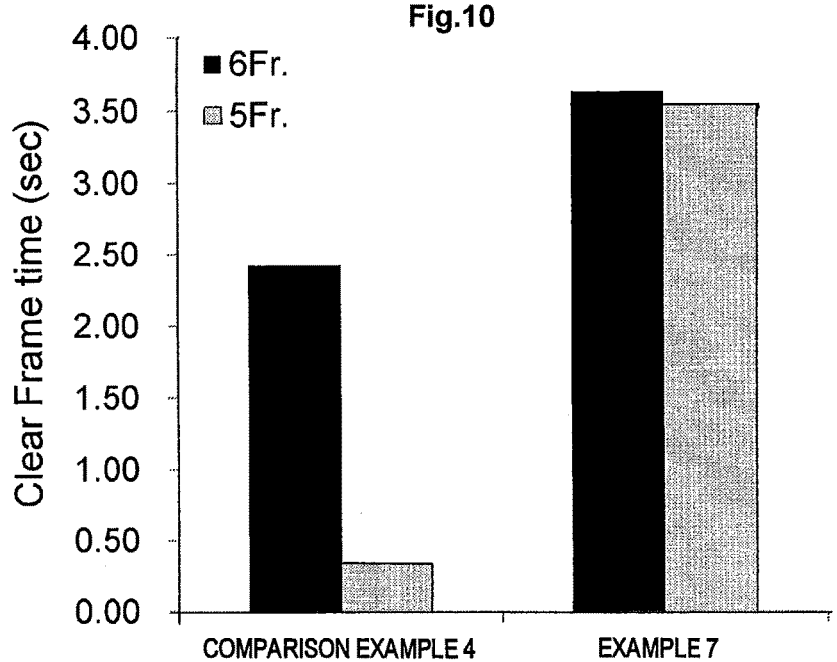

US 10,376,601 B2

IN-VIVO INTRAVASCULAR BLOOD REPLACING LIQUID, IN-VIVO INTRAVASCULAR BLOOD REPLACING LIQUID FORMULATION, AND PREFILLED SYRINGE

CROSS-REFERENCES TO RELATED APPLICATIONS

This application is a continuation of International Application No. PCT/JP2014/080001 filed on Nov. 12, 2014, which claims priority to Japanese Application No. 2014-070571 filed on Mar. 28, 2014, the entire contents of both of which is incorporated herein by reference.

TECHNICAL FIELD

The present invention relates to an in-vivo intravascular blood replacing liquid to be used when the image of a vascular state is diagnosed, an in-vivo intra vascular blood replacing liquid formulation, and a prefilled syringe.

BACKGROUND ART

An intravascular diagnostic apparatus utilizing an optical technology has greatly progressed in recent years. As a representative example of apparatuses utilizing the optical technology, an optical coherence tomography (OCT) diagnostic apparatus is exemplified. By using this apparatus, it has become possible to observe the property and state (for example, cross section of blood vessel and its inner surface) of a blood vessel and in addition, visualize an image to be observed in three dimensions and quantify the property and state of the blood vessel. The optical coherence tomography diagnostic apparatus depicts the image of the inner surface of the blood vessel, based on light reflected from in-vivo tissues by inserting an optical fiber having a probe incorporating an optical lens and an optical mirror mounted at a front end thereof into the blood vessel and by emitting light into the blood vessel with an optical mirror disposed at the front end of the optical fiber radially scanning the inner surface of the blood vessel. In another known image diagnostic apparatus, an optical frequency domain imaging (OFDI) method called a next-generation OCT is used, as disclosed in Japanese Patent Application Laid-Open Publication No. 2011-206375 (patent document 1 proposed by the present applicant).

When the intravascular image diagnosis is conducted, a catheter for use in the intravascular image diagnosis is delivered to a portion to be observed through a guide wire, In performing the intravascular image diagnosis, reflection of light and ultrasonic waves may occur owing to blood containing blood cell components such as red blood cells, which hinders the formation of tomographic and inner surface images of a blood vessel to be diagnosed with high accuracy. Thus in performing the intravascular image diagnosis, it is necessary to remove the blood cell components from the blood vessel to be diagnosed.

At a clinical site, image diagnosis is carried out after a state in which the blood cell components are removed from the blood vessel is temporarily produced by injecting a liquid such as a contrast agent having a high viscosity or saline into the blood vessel. All operation of discharging the liquid to the blood vessel is called a flush operation. The liquid discharged in the flush operation is so-called a flush solution.

PRIOR ART DOCUMENTS

Patent Documents

Patent document 1: Japanese Patent Application Laid-Open Publication No. 2011-206375

SUMMARY OF THE INVENTION

Problems to be Solved by the Invention

As described above, in a case where the saline is used as the flush solution, the duration of blood discharge is short. Thus it is impossible to measure the property and state of blood vessel. In other words, it is impossible to accomplish image diagnosis. The use of the contrast agent as the flush solution may cause a side effect represented by contrast nephropathy. Thus a decrease of the amount of the contrast agent is demanded. Because the flush solution is injected into the blood vessel through a guiding catheter, the viscosity of the flush solution greatly affects an injection resistance force. The resistance to the injection of the flush solution is greatly affected by the inner diameter of the catheter serving as the flow path of the flush solution. When the resistance to the injection of the flush solution is excessively high, there is a possibility that the flush solution is defectively injected into the blood vessel.

Therefore it is an object of the present invention to provide an in-vivo intravascular blood replacing liquid which eliminates the need for the use of a contrast agent, is subjected to a low injection resistance, and has a sufficient degree of blood immunity and continuity to some extent, an in-vivo intravascular blood replacing liquid formulation, and a prefilled syringe.

Means for Solving the Problems

The means for achieving the above-described object of the present invention is as described below.

In making an in-vivo intravascular inspection, an in-vivo intravascular blood replacing liquid is injected into a blood vessel to replace blood at an in-vivo intravascular portion to be inspected therewith. The blood replacing liquid comprises an aqueous medium unharmful for a living body and a gelling property imparting substance, unharmful for the living body, which is added to the aqueous medium to impart a gelling property to the blood replacing liquid. The blood replacing liquid has a viscosity of not more than 3 mPa·s when the blood replacing liquid is injected into the blood vessel

BRIEF DESCRIPTION OF THE DRAWINGS

FIG. 9 is a graph showing experimental results.

FIG. 10 is a graph showing experimental results.

MODE FOR CARRYING OUT THE INVENTION

Figure 1:
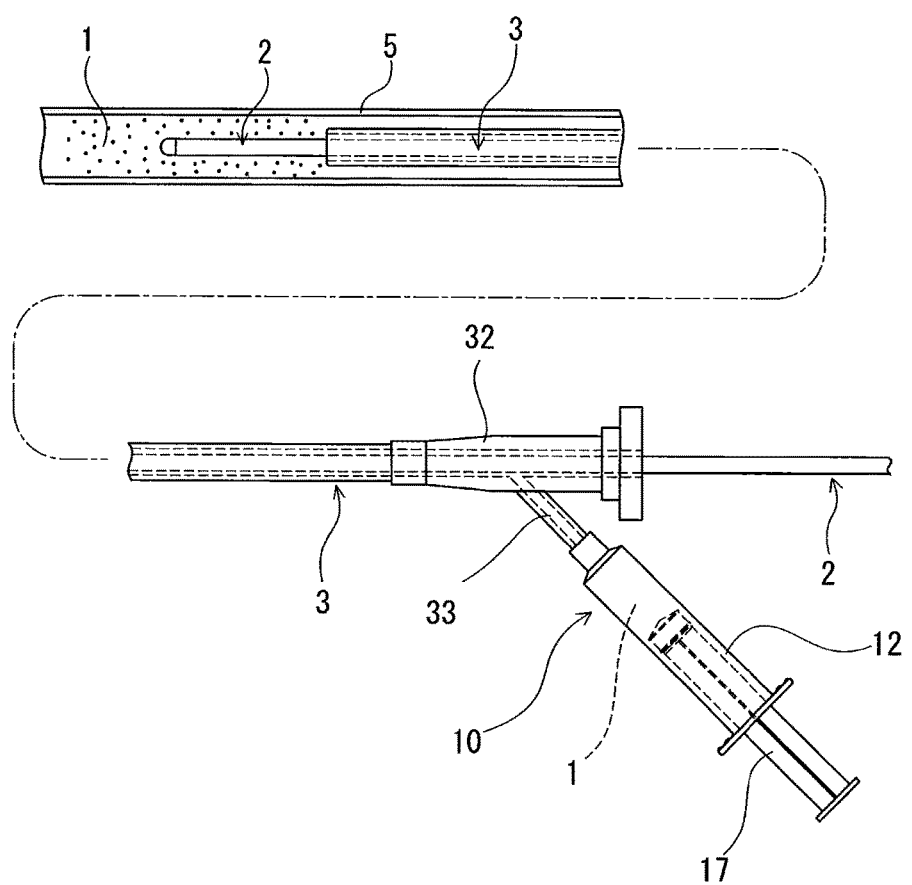
FIG. 1 is an explanatory view for explaining a state in which an in-vivo intravascular blood replacing liquid of the present invention is administered to a blood vessel.

An in-vivo intravascular blood replacing liquid of the present invention, an in-vivo intravascular blood replacing liquid formulation using it, and a prefilled syringe are described below with reference to embodiments.

In making an in-vivo intravascular inspection, an in-vivo intravascular blood replacing liquid 1 of the present invention is injected into a blood vessel to replace blood at an in-vivo intravascular portion to be inspected. The blood replacing liquid 1 comprises an aqueous medium unharmful for a living body and a gelling property imparting substance, unharmful for the living body, which is added to the aqueous medium to impart a gelling property to the blood replacing liquid. The viscosity of the blood replacing liquid is not more than 3 mPa·s when the blood replacing liquid is injected into the blood vessel.

The intravascular blood replacing liquid of the present invention can be easily prepared by adding an appropriate amount of the gelling property imparting substance to the aqueous medium and stirring the mixture of the aqueous medium and the gelling property imparting substance.

The in-vivo intravascular blood replacing liquid formulation of the present invention comprises a medical container and the above-described intravascular blood replacing liquid filled therein.

A prefilled syringe 10 in which the intravascular blood replacing liquid of the present invention has been filled comprises an outer cylinder 12, a gasket 16 slidably accommodated inside the outer cylinder 12, a sealing part 15 for sealing a front end portion of the outer cylinder 12, and the intravascular blood replacing liquid 1 filled inside the outer cylinder.

It is preferable to use the outer cylinder, the gasket, and the sealing part all subjected to sterilization in advance. The sterilizing method is not specifically limited. For example, it is possible to use filtration sterilization, a high-pressure steam sterilization method, a dry heating sterilization method, an ethylene oxide gas sterilization method, a radiation (for example, electron beam, x-ray, y-ray, and the like) sterilization method, a sterilization method to be carried out by using ozone water, and a sterilization method to be carried out by using a hydrogen peroxide solution.

As shown in FIG. 1, the in-vivo intravascular blood replacing liquid 1 and prefilled syringe 10 of the present invention are used by injecting the in-vivo intravascular blood replacing liquid into the blood vessel by using a tubular body (for example, catheter, probe) inserted into the in-vivo intravascular portion.

With reference to FIG. 1, a guiding catheter 3 is inserted into a blood vessel 5. An in-vivo insertion probe 2 for image diagnosis is inserted into the guiding catheter. The prefilled syringe 10 in which the intravascular blood replacing liquid has been filled is mounted on a side port 33 of a hub 32 of the guiding catheter 3. After a front end portion of the in-vivo insertion probe 2 for image diagnosis is disposed in the vicinity of the portion to be diagnosed, a plunger 17 of the prefilled syringe 10 mounted on the guiding catheter 3 is pressed into the prefilled syringe. Thereby the intra vascular blood replacing liquid 1 passes inside the guiding catheter 3 and is injected into the blood vessel from the front end thereof. Blood at the portion to be diagnosed is carried away by the intravascular blood replacing liquid 1 injected into the blood vessel. As a result, the portion where the intravascular blood replacing liquid has been injected is filled with the intravascular blood replacing liquid. Thereby it is possible to obtain information for blood vessel diagnosis by using the in-vivo insertion probe 2 for image diagnosis, without being adversely affected by the blood.

The in-vivo intravascular blood replacing liquid 1 of the present invention comprises the aqueous medium unharmful for the living body and the gelling property imparting substance, unharmful for the living body, which is added to the aqueous medium to impart the gelling property to the in-vivo intravascular blood replacing liquid.

As the aqueous medium, sterile water, saline, and a buffer solution are preferably used. As the sterile water, water for injection such as distilled water and RO water are preferable. The viscosity of the in-vivo intravascular blood replacing liquid 1 is favorably not more than 3 mPa·s and more favorably not more than 2 mPa·s at not more than 30 degrees C. It is also preferable that the in-vivo intravascular blood replacing liquid displays the gelling property at not less than 25 degrees C.

It has been regarded that a flush solution having a viscosity not less than 2 mPa·s is effective for removing blood. But as a result of investigations, it has been confirmed that even a liquid having a viscosity less than 2 mPa·s is capable of removing the blood, provided that the liquid has the gelling property.

It is preferable that the viscosity of the in-vivo intravascular blood replacing liquid is not more than 3 mPa·s at 30 degrees C. in the case of the in-vivo intravascular blood replacing liquid having the viscosity in the above-described range, an injection resistance is low in injecting it into the blood vessel and thus it can be easily injected thereinto.

The gelling property imparting substance is classified into substances displaying the function thereof as a single substance and substances displaying the function thereof by mixing not less than two kinds of compounds with each other.

The gelling property imparting substance which displays its function as a single substance is mucoperiosteum, a polysaccharide thickener, or a compound having a phosphate group, a carboxylic acid group or a sulfate group, More specifically, the above-gelling property imparting substances are possible to list glycyrrhizin acid, hyaluronic acid, chondroitin sulfate, alginic acid, ammonium sulfate, dextran sulfate, glucuronic acid, and salts or derivatives thereof.

As the gelling property imparting substances prepared by mixing not less than two kinds of compounds with each other, it is possible to exemplify those which gelate by chemical or physical interactions such as ionic bonds, hydrogen bonds or Van der Waals forces. As such gelling property imparting substances, it is possible to list mixtures of glycyrrhizin acids and basic amino acids or derivatives thereof, mixtures of chitin or chitosan or derivatives thereof and hyarulonic acid or derivatives thereof, and mixtures of chondroitin sulfate or derivatives thereof and basic compounds.

The gelling property imparting substance may be dissolved in a solvent in advance before it is mixed with the aqueous medium. Solvents which dissolve hydrophilic polymer therein are not specifically limited. But considering that it is necessary for the solvents to mix with water, water, alcohols, DMF, THF, and DMSO are desirable. Of these solvents, water is most desirable. Hydrophilic polymer having a molecular weight of 200 to 1000000 is favorable and those having a molecular weight of 400 to 40000 are especially favorable.

The in-vivo intravascular blood replacing liquid 1 may contain the hydrophilic polymer as a viscosity modifier thereof in a scope not departing from the spirit of the present invention. Although the kind of the hydrophilic polymer is not specifically limited, it is preferable that the hydrophilic polymer does not contain dextran and is water-soluble. The hydrophilic polymer has a structure in which monomers having the same structure are repeatedly arranged. In consideration of the background of a disease, a compound containing hydrophilic polymer which are directly decomposed into glucose in the liver and increase a blood glucose level is undesirable. As the hydrophilic polymer belonging to this category, dextran is known.

Examples of the hydrophilic polymer of the present invention include gelatin, methylcellulose, polyvinylpyrrolidone, polyethylene glycol, ficoll, polyvinyl alcohol, styrene-maleic anhydride alternating copolymers, divinyl ether-maleic anhydride alternating copolymers, polvvinylpyrrolidone, polyvinyl methyl ether, polyvinyl methyl oxazoline, poly ethyl oxazoline, poly hydroxypropyl oxazoline, poly hydroxypropyl methacrylamide, polymethacrylamide, polydimethylacrylamide, poly hydroxypropyl methacrylate, polyhydroxyethyl acrylate, hydroxymethyl cellulose, hydroxyethyl cellulose, polyaspartamide, and synthetic polyamino acid.

The hydrophilic polymer may be dissolved in a solvent in advance before the polymer is mixed with the aqueous medium. Solvents which dissolve the hydrophilic polymer therein are not specifically limited. But considering that it is necessary for the solvent to mix with water, water, alcohols, DMF, THF, and DMSO are desirable. Of these solvents, water is most desirable. Hydrophilic polymer having a molecular weight of 200 to 1000000 is favorable and those having a molecular weight of 400 to 40000 are especially favorable.

In the present invention, by selecting appropriate hydrophilic polymer, it is possible to obtain the in-vivo intravascular blood replacing liquid having a viscosity of not less than 2 mPa·s. In this case, it is conceivable that the in-vivo intravascular blood replacing liquid does not contain the gelling property imparting substance.

The in-vivo intravascular blood replacing liquid of a type not containing the gelling property imparting substance is described below.

In making the in-vivo intravascular inspection, the in-vivo intravascular blood replacing liquid of the embodiment is injected into the blood vessel to replace blood at the in-vivo intravascular portion to be inspected therewith. The blood replacing liquid is a transparent aqueous liquid consisting of the aqueous medium unharmful for the living body and the hydrophilic polymer added to the aqueous medium to enhance the viscosity of the blood replacing liquid.

Because the viscosity of the intravascular blood replacing liquid depends on the concentration (addition amount) of the hydrophilic polymer, it is easy to design the viscosity of the intravascular blood replacing liquid. Thus it is easy to prepare the intravascular blood replacing liquid having a preferable viscosity. In addition, the intravascular blood replacing liquid of this embodiment can be easily prepared by adding an appropriate amount of the hydrophilic polymer to the aqueous medium and stirring the mixture of these substances.

The in-vivo intra vascular blood replacing liquid formulation of this embodiment comprises the medical container and the intravascular blood replacing liquid filled therein.

Figure 2:
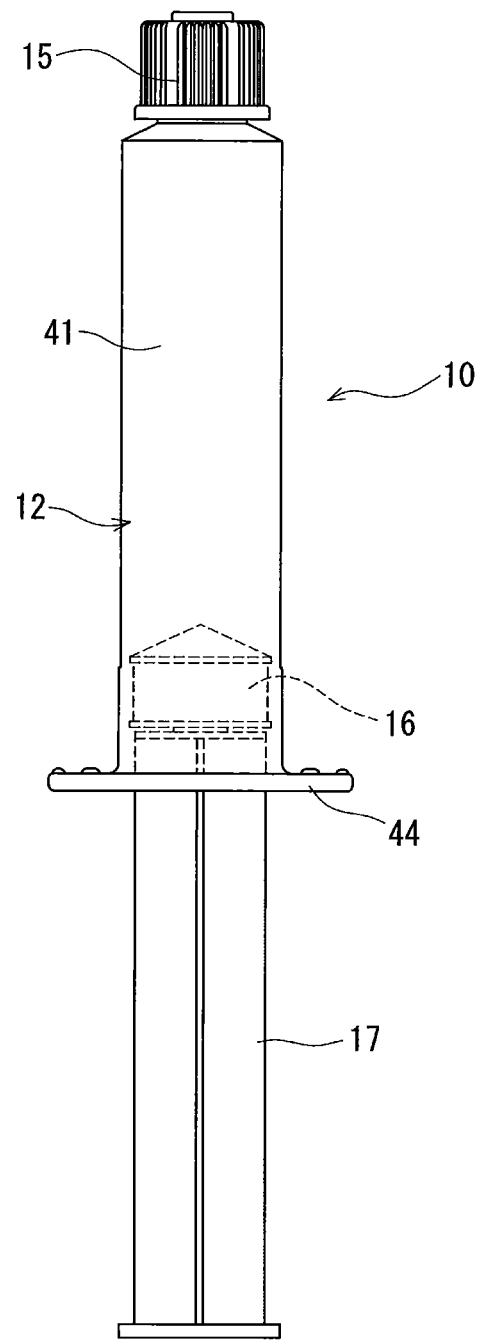
FIG. 2 is a front view of a prefilled syringe of the present invention.
Figure 3:
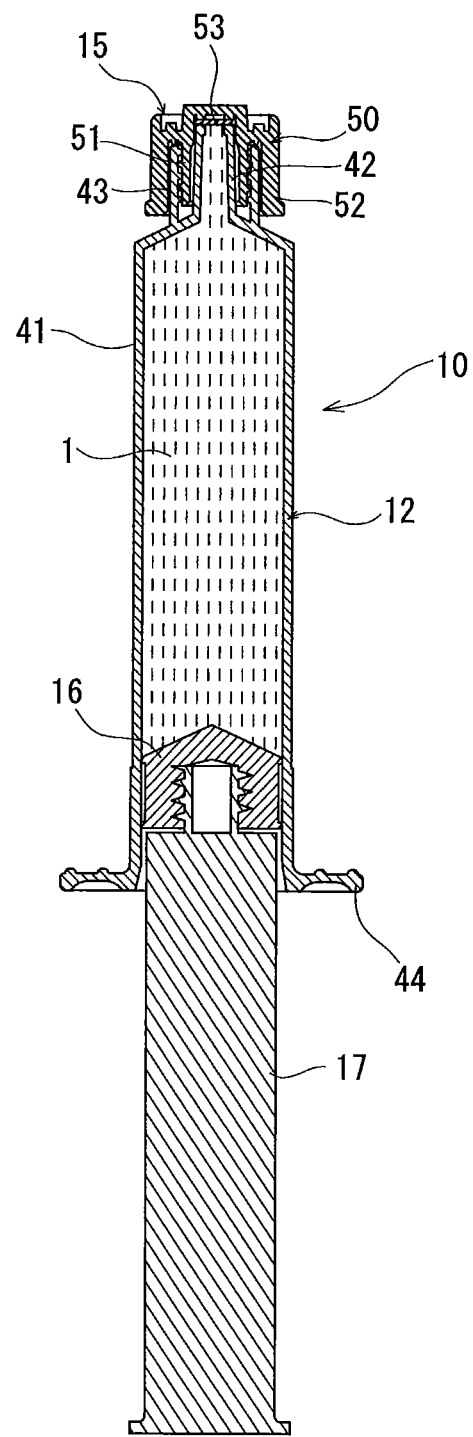
FIG. 3 is a vertical sectional view of the prefilled syringe shown in FIG. 2.

As with the prefilled syringe shown in FIGS. 2 and 3, the prefilled syringe of this embodiment in which the intravascular blood replacing liquid has been filled comprises the outer cylinder 12, the gasket 16 slidably accommodated inside the outer cylinder 12, the sealing part 15 for sealing the front end portion of the outer cylinder, and the intravascular blood replacing liquid 1.

It is preferable to use the outer cylinder, the gasket, and the sealing part all subjected to sterilization in advance. The sterilizing method is not specifically limited. For example, it is possible to use filtration sterilization, a high-pressure steam sterilization method, a dry heating sterilization method, an ethylene oxide gas sterilization method, a radiation (for example, electron beam, x-ray, y-ray, and the like) sterilization method, a sterilization method to be carried out by using ozone water, and a sterilization method to be carried out by using a hydrogen peroxide solution.

As with the above-described embodiment, the prefilled syringe and the in-vivo intravascular blood replacing liquid of the present invention are used by injecting the in-vivo intravascular blood replacing liquid into the blood vessel by using the tubular body (for example, catheter, probe) inserted into the in-vivo intravascular portion. Thereby it is possible to obtain information for blood vessel diagnosis by the in-vivo insertion probe 2 for image diagnosis without being adversely affected by blood.

The in-vivo intravascular blood replacing liquid 1 of this embodiment comprises the aqueous medium unharmful for the living body and the hydrophilic polymer added to the aqueous medium to enhance the viscosity of the in-vivo intravascular blood replacing liquid. Although the kind of the hydrophilic polymer is not specifically limited, it is preferable that the hydrophilic polymer does not contain dextran and is water-soluble.

The hydrophilic polymer of the present invention has the structure in which monomers having the same structure are repeatedly arranged. In consideration of the background of a disease, a compound containing the hydrophilic polymer which are directly decomposed into glucose in the liver and increase the blood glucose level is undesirable. As the hydrophilic polymer belonging to this category, dextran is known.

Examples of the hydrophilic polymer of the present invention include polyethylene glycol, ficoll, polyvinyl alcohol, styrene-maleic anhydride alternating copolymers, divinyl ether-maleic anhydride alternating copolymers, polyvinylpyrrolidone, polyvinyl methyl ether, polyvinyl methyl oxazoline, poly ethyl oxazoline, poly hydroxypropyl oxazoline, poly hydroxypropyl methacrylamide, polymethacrylamide, polydimethylacrylamide, poly hydroxypropyl methacrylate, polyhydroxyethyl acrylate, hydroxymethyl cellulose, hydroxyethyl cellulose, polyaspartamide, and synthetic polyamino acid.

The hydrophilic polymer may be dissolved in a solvent in advance before the hydrophilic polymer is mixed with the aqueous medium. Solvents which dissolve the hydrophilic polymer are not specifically limited. But considering that it is necessary for the solvents to mix with water, water, alcohols, DMF, THF, and DMSO are desirable. Of these solvents, water is most desirable. As the aqueous medium, sterile water, saline, and a buffer solution are used. As the sterile water, distilled water and RO water are used. Hydrophilic polymer having a molecular weight of 200 to 1000000 is favorable and those having a molecular weight of 400 to 40000 are especially favorable.

The viscosity of the in-vivo intravascular blood replacing liquid is favorably 2 to 100 mPa·s and especially favorably 3 to 10 mPa·s. In a case where the viscosity thereof is not less than 2 mPa·s, it is possible to impart a viscosity to some extent to the in-vivo intravascular blood replacing liquid and allow it to stay in the blood vessel for a certain period of time after it is injected into the blood vessel. In a case where its viscosity is not more than 100 mPa·s, it does not stay in the blood vessel for an excessively long period of time.

Although the concentration of the hydrophilic polymer of the in-vivo intravascular blood replacing varies according to the kind and molecular weight of the hydrophilic polymer to be used, the concentration thereof is not specifically limited so long as the concentration thereof allows the in-vivo intravascular blood replacing liquid to have the viscosity in the above-described range.

It is preferable that the intravascular blood replacing liquid of this embodiment does not substantially contain substances other than the above-described aqueous medium and the polyvinylpyrrolidone. As the intra vascular blood replacing liquid of this embodiment, it is preferable that the aqueous medium is sterile water and does not substantially contain substances other than the polyvinylpyrrolidone.

The in-vivo intravascular blood replacing liquid formulation of the present invention comprises the medical container and the above-described intravascular blood replacing liquid filled therein. As the medical container, it is possible to use a container for transfusion such as a soft bag, a pouch container, a plastic bottle; a vial, an ample, and a prefilled syringe. As the intravascular blood replacing liquid, any type of the above-described ones may be used.

As the container to be used to fill the intravascular blood replacing liquid. of the present invention therein, it is possible to use containers satisfying regulations demanded in each country.

As the container to be used to fill the intravascular blood replacing liquid of the present invention therein, it is possible to use the above-described medical containers generally used. In view of the use of the intra vascular blood replacing liquid of the present invention, a prefilled syringe formulation which is described later is preferable.

In a case where the medical container is a bag, it is preferable that the material thereof comprises various resins such as polypropylene, polyethylene, polystyrene, polyamide, polycarbonate, poly vinyl chloride, poly-(4-methylpentene-1), acrylic resin, an acrylonitrile-butadiene-styrene copolymer, polyester including polyethylene terephthalate; and cyclic polyolefins. In a case where a bag is selected as the container for the intravascular blood replacing liquid, it is necessary to transfer the intravascular blood replacing liquid to a syringe at a medical front. The material to be selected for the outer cylinder of the syringe is not specifically limited. It is possible to preferably use the outer cylinder of the syringe formed of any of various resins such as polypropylene, polyethylene, polystyrene, polyamide, polycarbonate, polyvinyl chloride, poly-(4-methylpentene-1), acrylic resin, an acrylonitrile-butadiene-styrene copolymer, polyester including polyethylene terephthalate; cyclic olefin copolymers; and cyclic polyolefins.

As shown in FIGS. 1 through 3, the prefilled syringe 10 of the present invention in which the intra vascular blood replacing liquid has been filled comprises the outer cylinder 12, the gasket 16 slidably accommodated inside the outer cylinder 12, the sealing part 15 for sealing the front end portion of the outer cylinder 12, the intravascular blood replacing liquid 1 filled inside the outer cylinder, and the plunger 17 mounted on the gasket 16. It is preferable to subject the prefilled syringe 10 to heat sterilization with the intravascular blood replacing liquid being filled therein.

The outer cylinder 12 has an outer cylinder body part 41, a nozzle portion 42 formed at a front end portion of the outer cylinder body part 41, and a flange part 44 formed at a rear end portion of the outer cylinder body part 41.

The outer cylinder 12 is a tubular body formed of a transparent or semitransparent material. It is preferable that the material thereof has a low degree of oxygen permeability and hydrogen permeability.

The outer cylinder body part 41 is a substantially tubular part accommodating the gasket 16 liquid-tightly and slidably. The nozzle portion 42 is a tubular portion whose diameter is smaller than that of the outer cylinder body part 41. The diameter of the front end portion (shoulder portion) of the outer cylinder body part 41 decreases in a tapered configuration toward the nozzle portion 42, The outer cylinder 12 of this embodiment has a collar portion 43 surrounding the nozzle portion 42. The nozzle portion 42 is formed at the front end of the outer cylinder 12 and has an opening for discharging such as liquid medicine filled inside the outer cylinder at its front end. The diameter of the nozzle portion decreases in a tapered configuration toward its front end. The collar portion 43 is formed cylindrically and concentrically with the nozzle portion 42 in such a way as to surround the nozzle portion 42. A spiral groove portion engageable with a spiral projected portion formed on an outer circumferential surface of a nozzle portion accommodation part 51 of the seal cap 15 which is a seal member to be described later and with a projected portion formed at a rear end of the side port 33 of the guiding catheter 3 is formed on an inner circumferential surface of the collar portion 43. The flange part 44 is an elliptic donut-shaped disk part projected vertically to the outer cylinder 12 from the entire circumference of the rear end thereof. The flange part 44 has two opposed gripping portions having a wide width.

As materials for forming the outer cylinder 12, it is possible to list various resins such as polypropylene, polyethylene, polystyrene, poly amide, polycarbonate, polyvinyl chloride, poly-(4-methylpentene-1), acrylic resin, an acrylonitrile-butadiene-styrene copolymer, polyester including polyethylene terephthalate; and cyclic olefin copolymers; and cyclic polyolefins. Of these resins, the polypropylene, the cyclic olefin copolymers, and the cyclic polyolefins are preferable because these resins are easily moldable and heat-resistant.

The seal cap 15 serving as the seal member consists of a cap body part 50 and a seal member 53 accommodated inside the cap body part. As shown in FIG. 3, the cap body part 50 is formed in the shape of a cap and has a nozzle portion accommodation part 51, a collar portion accommodation part 52, and a seal member holding part formed on an inner surface of the nozzle portion accommodation part 51. The nozzle portion accommodation part 51 is a tubular part formed at a central portion of the seal cap 15 and is closed at one end thereof and open at the other end thereof. An inner diameter of the nozzle portion accommodation part 51 is substantially equal from its one end to its other end. The spiral projected portion engageable with the spiral groove portion formed on the inner circumferential surface of the collar portion 43 of the outer cylinder 12 is formed on the outer circumferential surface of the nozzle portion accommodation part 51.

As materials for forming the seal cap, it is possible to list various resins such as polypropylene, polyethylene, polystyrene, polyamide, polycarbonate, polyvinyl chloride, poly-(4-methylpentene-1), acrylic resin, an acrylonitrile-butadiene-styrene copolymer, polyester including polyethylene terephthalate; and cyclic polyolefins. As materials for forming the seal member 53, it is preferable to use natural rubber; and synthetic rubber such as isoprene rubber, butadiene rubber, fluororubber, and silicone rubber; and thermoplastic elastomers such as olefin-based elastomers and styrene-based elastomers.

As shown in FIGS. 2 and 3, the gasket 16 has a body part extended substantially equally in its outer diameter and a plurality of annular ribs (in this embodiment, two annular ribs are formed) formed on the body part of the gasket. The annular ribs liquid-tightly contact an inner surface of the outer cylinder 12. A front end surface of the gasket 16 has a configuration corresponding to that of the inner surface of the front end of the outer cylinder 21 so as to prevent a gap from being formed as much as possible between the front end surface of the gasket and the inner surface of the front end of the outer cylinder when both surfaces contact each other. The gasket 16 has a plunger mounting part on its rear end portion. In this embodiment, the plunger mounting part is constructed of a concave portion extended inward from the rear end portion of the gasket and a female screw portion formed on an inner surface of the concave portion.

As a material for forming the gasket 16, it is preferable to use elastic rubber (for example, butyl rubber, latex rubber, silicone rubber) or synthetic resin (for example, styrene elastomer such as SBS elastomer, SEBS elastomer; and polyolefin elastomer such as ethylene-α-olefin copolymer).

The plunger 17 has a projected portion tubularly projected from its front end. A male screw portion which engages the concave portion of the gasket 16 is formed on an outer surface of the projected portion. The plunger 17 has a sectionally cross-shaped body part axially extended and a pressing disk part formed at a rear end portion thereof. In this embodiment, although the plunger 17 is mounted on the gasket in advance, the form of the plunger is not limited to that. The plunger may be mounted on the gasket when the prefilled syringe is used.

Description is made below Gil a guiding catheter and an in-vivo insertion probe for image diagnosis for which the in-vivo intravascular blood replacing liquid of the present invention is used.

The guiding catheter and the in-vivo insertion probe for image diagnosis shown in the drawings are examples and not limited to the form described below.

Figure 4:
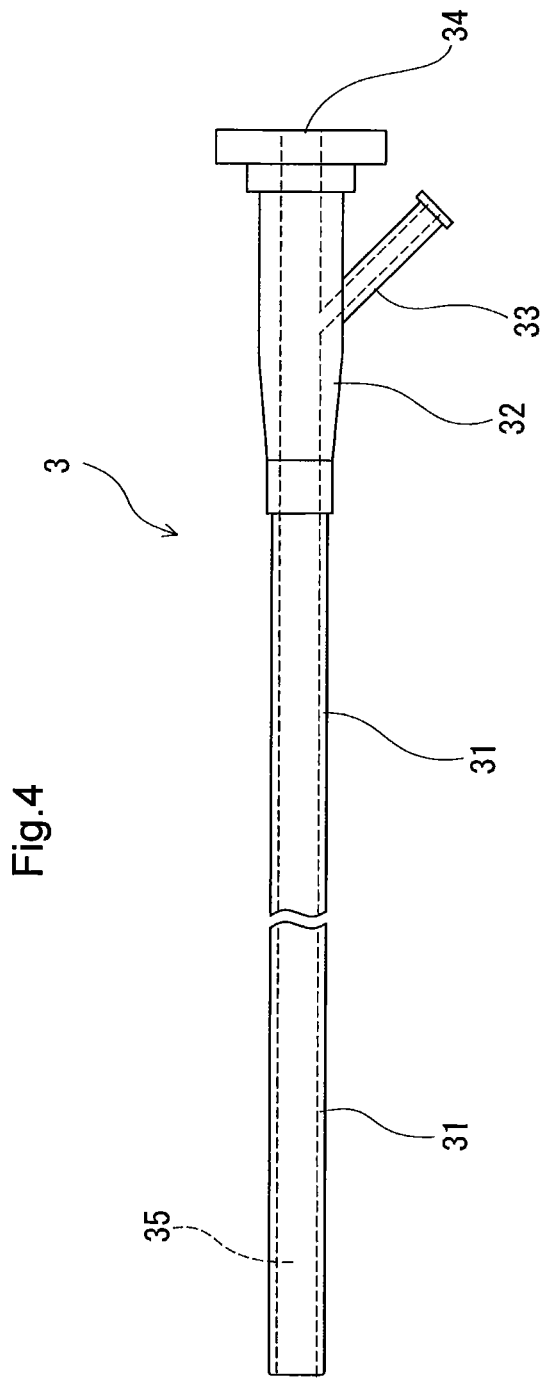
FIG. 4 is a front view of a guiding catheter to which the prefilled syringe of the present invention can be connected.

The guiding catheter 3 shown in FIG. 4 is composed of a catheter tube 31 which is hollow and has a predetermined length and a branch hub 32 mounted on a rear end portion of the catheter tube 31. The catheter 3 has a lumen 35 extended from a front end of the catheter tube 31 to an open portion 34 of the branch hub 32. The open portion 34 of the branch hub 32 is used as an insertion opening for the in-vivo insertion probe for image diagnosis. The side port 33 of the branch hub 32 is used as a connection port to which the prefilled syringe 10 in which the intravascular blood replacing liquid has been filled is connected.

Figure 5:
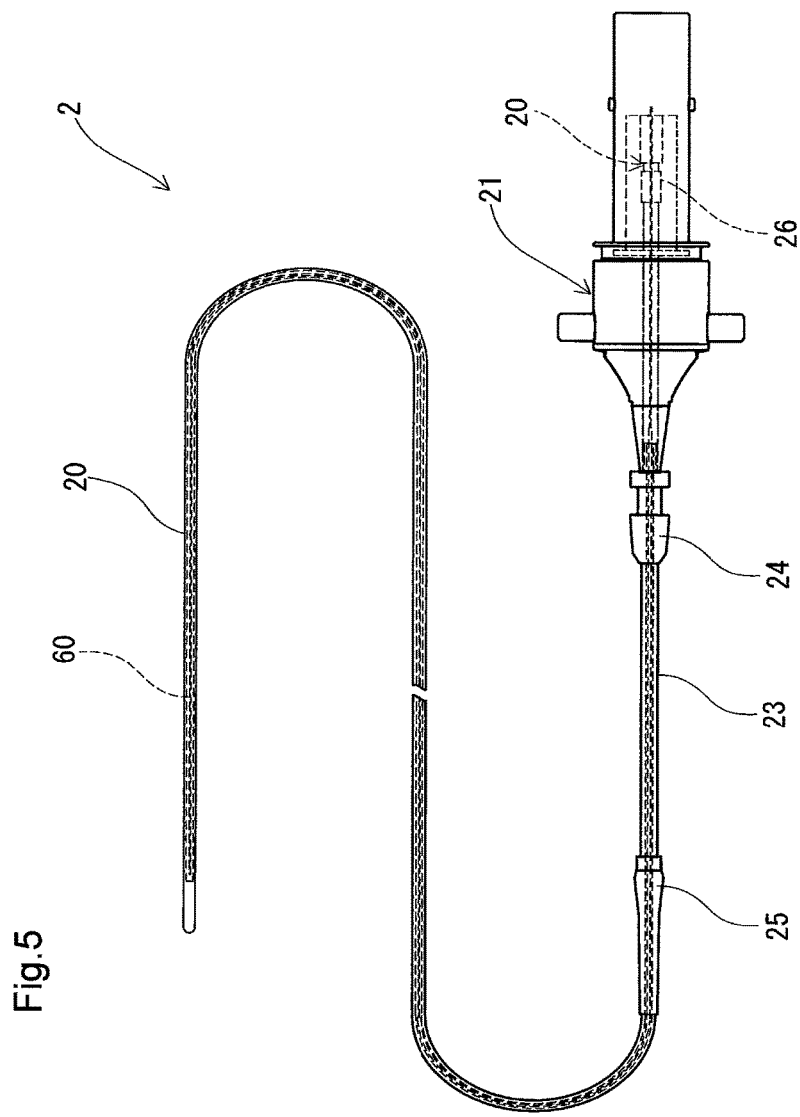
FIG. 5 is a front view of one example of an in-vivo insertion probe for an intravascular optical coherence tomography diagnostic apparatus for which the in-vivo intravascular blood replacing liquid of the present invention is used.
Figure 6:
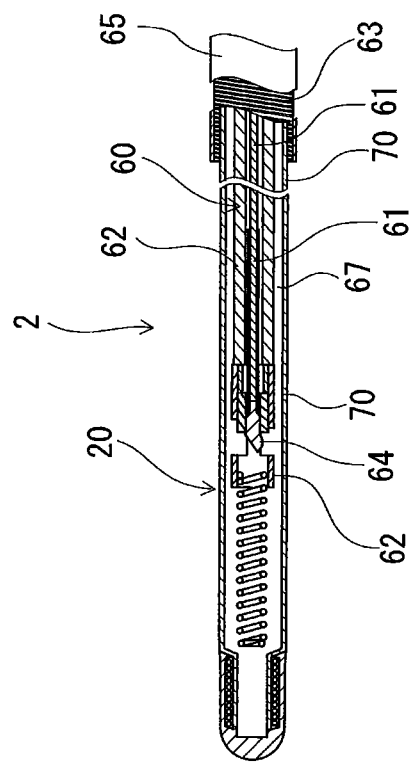
FIG. 6 is an enlarged vertical sectional view of a front end portion of the in-vivo insertion probe for the intravascular optical coherence tomography diagnostic apparatus shown in FIG. 5.

The in-vivo insertion probe for image diagnosis shown in FIGS. 5 and 6 comprises a sheath 20 to be inserted into a body cavity (inside guiding catheter) and a data acquisition shaft 60 inserted into the sheath 20. The data acquisition shaft 60 has a drive transmission shaft 62 and an optical fiber 61 penetrating through the hollow shaft 62 and having a chip portion 64 exposed from a front end portion of the hollow shaft 62. The data acquisition shaft 60 is rotated by a rotational force imparted thereto at a proximal portion thereof.

The optical in-vivo insertion probe 2 of this embodiment has the data acquisition shaft 60, the sheath 20 for accommodating the data acquisition shaft, and an operation member 21 through which the data acquisition shaft penetrates and which is positioned nearer to the proximal end of the optical in-vivo insertion probe than the sheath 20.

The sheath 20 is a tubular body closed at its front end and has a shaft lumen 67, extended from the proximal end of the sheath toward the front end thereof, for accommodating the data acquisition shaft. The sheath 20 has a sheath tube, a kink-resistant protector 25 disposed at a proximal end of the sheath tube, a base portion tube 23 fixed to a proximal portion of the protector 25, and a tube hub 24 fixed to a proximal end of the base portion tube 23.

In the in-vivo insertion probe 2 of this embodiment, the sheath tube is constructed of an inner tube 70, an intermediate tube 63, and an outer tube 65. The protector 25 is fixed to the proximal portion of the sheath tube. The base portion tube 23 extended to the proximal side of the optical in-vivo insertion probe by a predetermined length is fixed to the proximal portion of the protector 25. The tube hub 24 is fixed to the proximal portion of the base portion tube 23.

As shown in FIGS. 5 and 6, the data acquisition shaft 60 has the drive transmission shaft 62, the optical fiber 61 penetrating through the hollow shaft 62 and having the chip portion 64 exposed from the front end portion of the hollow shaft 62, a connector connected to a proximal portion of the optical fiber 61, and a connection member 26 connecting a proximal portion of the hollow shaft 62 and the connector to each other. The data acquisition shaft 60 is rotated by the rotational force imparted thereto by the connector. The drive transmission shaft 62 is a hollow body extended by a predetermined length and has an inner lumen portion penetrating therethrough from its proximal end to its front end. The inner lumen portion is capable of accommodating the optical fiber. As the drive transmission shaft 62, is possible to use a coil, a round wire or a flat metal wound in a single layer or a multilayer in the form of a coil or a blade, and a resin tube coated with a metallic rigidity imparting body or embedded therein.

As the optical fiber 61, it is possible to use a known solid optical fiber which can be extended by a predetermined length. As the optical fiber, for example, a single mode optical fiber can be used. It is preferable to coat an outer surface of a clad of the optical fiber with a resin material called jacket. As shown in FIG. 6, a chip portion 64 is optically connected to the front end of the optical fiber 61. In the in-vivo insertion probe of this embodiment, a lens is used as the chip portion 64.

The method of using the in-vivo intravascular blood replacing liquid of the present invention is described below.

The in-vivo insertion probe 2 is used by connecting a proximal portion (connector portion of data acquisition shaft and proximal portion of operating holding member of operation member 21) thereof to an external device (not shown).

The external device is connected to the connector of the data acquisition shaft, and has a driving source for rotating the data acquisition shaft at a high speed, an optical source for supplying light to the optical fiber of the data acquisition shaft, and an image display function of forming an image by using light sent from the chip portion (lens portion) of the data acquisition shaft.

In using the in-vivo insertion probe, by using the guiding catheter where the in-vivo insertion probe 2 whose proximal portion has been connected to the external device is inserted, the in-vivo insertion probe is inserted into an intravascular portion to be diagnosed. As shown in FIG. 1, by using the prefilled syringe connected to the branch hub of the guiding catheter 3, the intravascular blood replacing liquid is injected into a blood vessel. Thereby blood at the intravascular portion disposed forward by a predetermined interval from the guiding catheter is carried away by the in-vivo intravascular blood replacing liquid. As a result, the intravascular portion to be diagnosed is filled with the in-vivo intravascular blood replacing liquid. Thereafter the external device is driven to rotate the data acquisition shaft. Then in-vivo information is obtained from the chip portion rotating together with the shaft. In performing axial scan by means of the in-vivo insertion probe, the probe is moved axially at the intravascular portion to be diagnosed. Thereby new in-vivo information can be obtained.

Description is made below on another example of the in-vivo insertion probe for image diagnosis for which the in-vivo intravascular blood replacing liquid of the present invention is used.

An in-vivo insertion probe 100 of this embodiment is constructed by applying the in-vivo insertion probe of the present invention to an ultrasonic in-vivo insertion probe.

Figure 7:
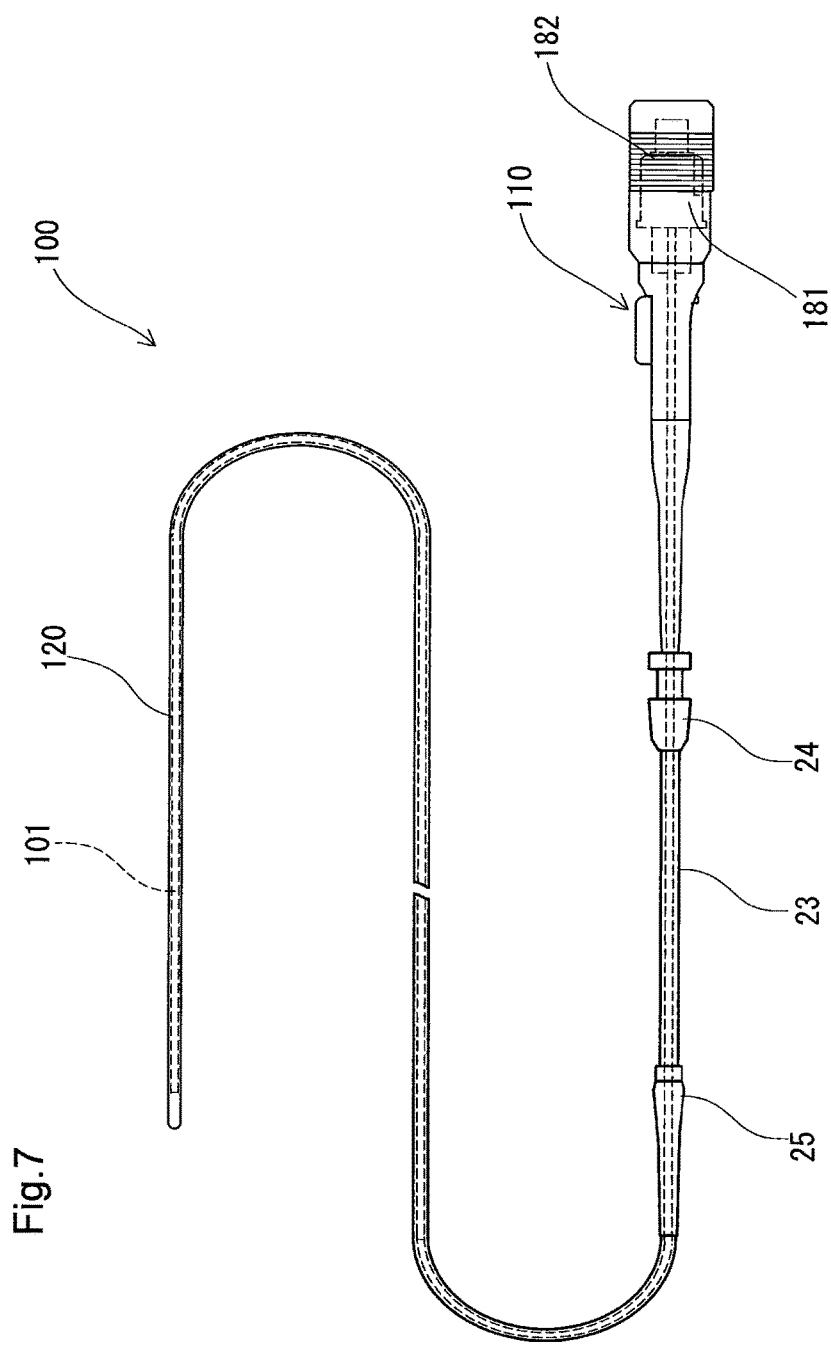
FIG. 7 is a front view of one example of an in-vivo insertion probe for an intravascular ultrasonic diagnostic apparatus for which the in-vivo intravascular blood replacing liquid of the present invention is used.

As shown in FIG. 7, the ultrasonic in-vivo insertion probe 100 of this embodiment comprises a sheath 120 to be inserted into a body cavity and a data acquisition shaft 101 inserted into the sheath 120. The sheath 120 is the same as that described above.

The data acquisition shaft 101 of this embodiment has a drive transmission hollow shaft 102, an ultrasonic vibrator 104 fixed to a front end portion of the hollow shaft 102, and a connector 110 connectable to a connection portion of an external device. The data acquisition shaft 101 is rotated by a rotational force imparted thereto by the connector 110.

Figure 8:
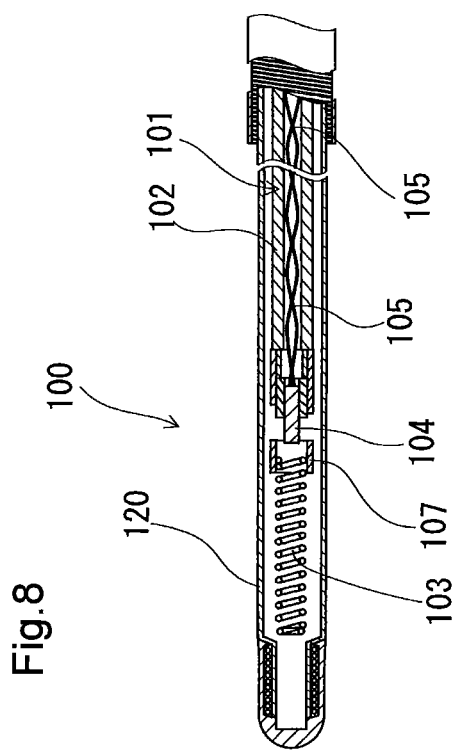
FIG. 8 is an enlarged vertical sectional view of a front end portion of the in-vivo insertion probe for the intravascular ultrasonic diagnostic apparatus shown in FIG. 7.

As shown in FIG. 8, as a chip portion, a transducer 104 having the function of an ultrasonic vibrator for sending and receiving ultrasonic waves is used for the data acquisition shaft 101. The data acquisition shaft 101 has a transducer housing 107 for accommodating the transducer 104 at its front end portion. The housing 107 is a tubular body having an open portion for exposing the transducer 104. The housing is fixed to the front end portion of the hollow shaft 102 at its proximal portion. A rotation stabilization member 103 extended toward the front end of the ultrasonic in-vivo insertion probe is mounted on a front end portion of the housing 107. As the rotation stabilization member, a coiled body as shown in figure is preferable. The drive transmission hollow shaft 102 is a hollow body having a predetermined length and a lumen penetrating therethrough from its proximal end to its front end.

As shown in FIG. 8, the hollow shaft 102 incorporates a signal line 105 consisting of two twisted lead wires. A front end of the signal line 105 is connected to a vibrator of the transducer 104. A rear end of the signal line 105 is connected to a receptacle (not shown) of the connector 110. The connector 110 has a connector housing 181 and an annular elastic member 182 provided on an outer surface of the connector housing. The data acquisition shaft 101 of the in-vivo insertion probe 100 of this embodiment also rotates.

The external driving device (not shown) to which the in-vivo insertion probe 100 is connected has a function of picking up signals transmitted from a driving source including a motor and the probe. The external driving device is electrically connected to a console having a sending and receiving circuits and an image display device.

As with the above-described image diagnosis to be performed by using light, the in-vivo intravascular blood replacing liquid of the present invention is used for the image diagnosis to be performed by using ultrasonic waves.

EXAMPLES

1. The following substances were prepared as additives.
1) Glycyrrhizin acid monoammonium (GLZA): produced by Maruzen Pharmaceuticals Co., Ltd.
2) Gelatin: produced by Jellice Co., Ltd.
3) Polyvinylpyrrolidone: molecular weight 40,000, produced by Sigma-Aldrich Corporation
4) Thiamine chloride hydrochloride: produced by DSM Japan K.K.
5) Polyethylene glycol 400: molecular weight 400 PEG400 (brand name), produced by Kanto Chemical Co., Inc.
2. The following apparatuses were prepared:
1) OFDI intravascular image diagnosis apparatus: LUNA-WAVE (registered trademark) produced by Terumo Corporation
2) Guiding catheter (6Fr, 5Fr): Heartrail (registered trademark) produced by Terumo Corporation
3) Guide wire: Runthrough (registered trademark) produced by Terumo Corporation
4) in-vivo insertion probe for image diagnosis: FirstView (registered trademark) produced by Terumo Corporation
3. A lactic acid buffer solution was prepared as follows:
6.0 g of sodium chloride, 0.3 g of potassium chloride, 0.2 g of calcium chloride dehydrate, and 6.2 g of an L-sodium lactate solution were weighed. Water was added to the mixture of the above-described substances to dissolve them therein. Thereafter water was added to the solution to set the volume thereof to 1 L.
4. A glucose sodium chloride solution was prepared as follows:
After 4.0 g of glucose and 0.9 g of sodium chloride were weighed, water was added to the mixture to set the volume of the solution to 200 mL.
5. A thiamine chloride hydrochloride solution was prepared as follows:
1 g of the thiamine chloride hydrochloride was dissolved in water to set the volume of the solution to 100 mL to form the thiamine chloride hydrochloride solution.

EXAMPLES AND COMPARISON EXAMPLES

An in-vivo intravascular blood replacing liquid (flush solution) of each of the examples and comparison examples was formed or prepared.

Example 1

The lactic acid buffer solution was added to gelatin to dissolve the gelatin therein. The in-vivo intravascular blood replacing liquid (flush solution) was prepared by adjusting the concentration of the gelatin to 1 mg/mL. The viscosity of the flush solution at 25 degrees C. was 1.0 mPa·s.

Example 2

The lactic acid buffer solution was added to the gelatin to dissolve the gelatin therein. The in-vivo intravascular blood replacing liquid (flush solution) was prepared by adjusting the concentration of the gelatin to 2 mg/mL. The viscosity of the flush solution at 25 degrees C. was 1.0 mPa·s.

Example 3

The lactic acid buffer solution was added to the gelatin to dissolve the gelatin therein. The in-vivo intravascular blood replacing liquid (flush solution) was prepared by adjusting the concentration of the gelatin to 4 mg/mL. The viscosity of the flush solution at 25 degrees C. was 1.1 mPa·s.

Example 4

The lactic acid buffer solution was added to the weighed amount of glycyrrhizin acid monoammonium to prepare a solution of 0.05 mg/mL. A thiamine chloride hydrochloride solution was added to the glycyrrhizin acid monoammonium solution in such a way that the molar ratio between the glycyrrhizin acid monoammonium and the thiamine was 1:1. In this manner, the in-vivo intravascular blood replacing liquid (flush solution) was formed. The viscosity of the flush solution at 25 degrees C. was 1.0 mPa·s.

Example 5

The lactic acid buffer solution was added to the weighed amount of glycyrrhizin acid monoammonium to prepare a solution of 0.10 mg/mL. The thiamine chloride hydrochloride solution was added to the glycyrrhizin acid monoammonium solution in such a way that the molar ratio between the glycyrrhizin acid monoammonium and the thiamine was 1:1. In this manner, the in-vivo intravascular blood replacing liquid (flush solution) was formed.

The viscosity of the flush solution at 25 degrees C. was 1.0 mPa·s.

Example 6

The lactic acid buffer solution was added to the weighed amount of glycyrrhizin acid monoammonium to prepare a solution of 0.20 mg/mL. The thiamine chloride hydrochloride solution was added to the glycyrrhizin acid monoammonium solution in such a way that the molar ratio between the glycyrrhizin acid monoammonium and the thiamine was 1:1. In this manner, the in-vivo intravascular blood replacing liquid (flush solution) was formed. The viscosity of the flush solution at 25 degrees C. was 1.0 mPa·s.

Example 7

The lactic acid buffer solution was added to the weighed amount of glycyrrhizin acid monoammonium to prepare a solution of 0.5 mg/mL. The thiamine chloride hydrochloride solution was added to the glycyrrhizin acid monoammonium solution in such a way that the molar ratio between the glycyrrhizin acid monoammonium and the thiamine was 1:1. In this manner, the in-vivo intravascular blood replacing liquid (flush solution) was formed. The viscosity of the flush solution at 25 degrees C. was 1.4 mPa·s.

Example 8

The lactic acid buffer solution was added to the weighed amount of glycyrrhizin acid monoammonium to prepare a solution of 1.0 mg/mL. The thiamine chloride hydrochloride solution was added to the glycyrrhizin acid monoammonium solution in such a way that the molar ratio between the glycyrrhizin acid monoammonium and the thiamine was 1:1. In this manner, the in-vivo intravascular blood replacing liquid (flush solution) was formed. The viscosity of the flush solution at 25 degrees C. was 1.7 mPa·s.

Example 9

By adding 50 mg of the gelatin to 50 mL of the flush solution of the example 4 and dissolving the gelatin in the flush solution, the in-vivo intravascular blood replacing liquid (flush solution) was formed. The viscosity of the flush solution at 25 degrees C. was 1.0 mPa·s.

Example 10

By adding 100 mg of the gelatin to 50 mL of the flush solution of the example 4 and dissolving the gelatin in the flush solution, the in-vivo intravascular blood replacing liquid (flush solution) was formed. The viscosity of the flush solution at 25 degrees C. was 1.1 mPa·s.

Example 11

By adding 200 mg of the gelatin to 50 mL of the flush solution of the example 4 and dissolving the gelatin in the flush solution, the in-vivo intravascular blood replacing liquid (flush solution) was formed. The viscosity of the flush solution at 25 degrees C. was 1.1 mPa·s.

Example 12

By adding 1 g of PEG400 to 50 mL of the flush solution of the example 7 and dissolving the PEG400 in the flush solution, the in-vivo intravascular blood replacing liquid (flush solution) was formed. The viscosity of the flush solution at 25 degrees C. was 1.5 mPa·s.

Example 13

By adding 3 g of the PEG400 to 50mL of the flush solution of the example 7 and dissolving the PEG400 in the flush solution, the in-vivo intravascular blood replacing liquid (flush solution) was formed. The viscosity of the flush solution at 25 degrees C. was 1.5 mPa·s.

Example 14

By adding 6 g of the PEG400 to 50 mL of the flush solution of the example 7 and dissolving the PEG400 in the flush solution, the in-vivo intravascular blood replacing liquid (flush solution) was formed. The viscosity of the flush solution at 25 degrees C. was 1.7 mPa·s.

Comparison Example 1

As a comparison example 1, saline was used. The viscosity of the flush solution at 25 degrees C. was 1.0 mPa·s.

Comparison Example 2

As a comparison example 2, a lactate Ringer solution was used. The viscosity of the flush solution at 25 degrees C. was 1.0 mPa·s.

Comparison Example 3

The lactic acid buffer solution was added to the weighed amount of the glycyrrhizin acid monoammonium to prepare a solution of 0.20 mg/mL. In this manner, the flush solution was obtained. The viscosity of the flush solution at 25 degrees C. was 1.0 mPa·s.

Comparison Example 4

Low molecular weight dextran containing fluid (product name: "Otsuka Dextran L injection" produced by Otsuka Pharmaceutical Factory Co., Ltd.) having an average molecular weight of 40,000 was used to form the flush solution. The viscosity of the flush solution at 25 degrees C. was 4.8 mPa·s.

Comparison Example 5

Omnipaque 300 injection syringe (non-ionic contrast agent produced by Daiichi Sankyo Company, Ltd.) was prepared to form the flush solution. The viscosity of the flush solution at 20 degrees C. was 13.3 mPa·s.

Omnipaque 350 (non-ionic contrast agent produced by Daiichi Sankyo Company, Ltd.) was prepared to form the flush solution. The viscosity of the flush solution at 25 degrees C. was 26.7 mPa·s.

The viscosities of the flush solutions were measured by using a viscometer.

Experiment 1

Evaluation of In-Vitro Image Diagnosis

By using the intravascular blood replacing liquids (flush solutions) of the examples and comparison examples, evaluations of image diagnoses were conducted by using a model blood vessel. As the model blood vessel, the blood of a pig was applied to a silicone tube by using a constant flow rate pump. When a state in which the inner diameter of the silicone tube could be seen for not less than three seconds continued, image diagnoses were judged as good. Each flush solution was applied to the in-vivo insertion probe for image diagnosis and guide wire-inserted guiding catheters whose outer diameters were different from one another. A syringe pump was used to feed the flush solutions. The experimental conditions of the experiment were as follows:

Conditions in feeding flush solution:
Pig blood feeding speed: 250 mL; minute
Flush solution feeding speed: 150 mL/minute
Feeding amount of flush solution: 20 mL The results of the in vitro experiment made on the image diagnostic performance were as shown in table 1.

TABLE 1

| Flush solution | Viscosity (mPa · s) | Image diagnostic performance Guiding catheter: 6Fr | Image diagnostic performance Guiding catheter: 5Fr |
| --- | --- | --- | --- |
| Example 1 | 1.0 | Good | Good |
| Example 2 | 1.0 | Good | Good |
| Example 3 | 1.1 | Good | Good |
| Example 4 | 1.0 | Good | Good |
| Example 5 | 1.0 | Good | Good |
| Example 6 | 1.0 | Good | Good |
| Example 7 | 1.4 | Good | Good |
| Example 8 | 1.7 | Good | Good |
| Example 9 | 1.0 | Good | Good |
| Example 10 | 1.1 | Good | Good |
| Example 11 | 1.1 | Good | Good |
| Example 12 | 1.5 | Good | Good |
| Example 13 | 1.5 | Good | Good |
| Example 14 | 1.7 | Good | Good |
| Comparison example 1 | 1.0 | Bad | Bad |
| Comparison example 2 | 1.0 | Bad | Bad |
| Comparison example 3 | 1.0 | Bad | Bad |
| Comparison example 4 | 4.8 | Good | Bad |
| Comparison example 5 | 13.3 | Good | Bad |
| Comparison example 6 | 26.7 | Good | Bad |

As shown in table 1, the flush solutions of all of the examples 1 through 14 allowed images to be seen clearly for not less than five seconds after the flush solutions were applied to the in-vivo insertion probe and the guiding catheters. Thus the flush solutions of the present invention proved to be effective. On the other hand, although the flush solutions of the comparison examples 1 through 3 had the viscosity equal to those of the flush solutions of the examples 1 through 6, the image diagnostic performance was evaluated as bad. Therefore it is conceivable that the flush solutions examined and devised in the present invention achieved good image diagnostic performance owing to a factor different from the viscosity.

The flush solutions of the comparison examples 4 through 6 are now commonly used in angiography to be performed by using OFDI. Evaluations were made on the image diagnoses conducted in the use of the flush solutions. As a result, in the examples in which the guiding catheter of 6Fr was used, good image diagnostic performance was shown, whereas in the examples in which the guiding catheter of 5Fr was used, good image diagnostic performance was not obtained. Conceivably, because the viscosities of the flush solutions were high, an intended speed could not be achieved or an intended amount of the flush solutions could not be injected into the blood vessel. On the other hand, it was confirmed that the flush solutions of the present invention having low viscosities allowedgood image diagnostic performance to be obtained in the use of the guiding catheter of 5Fr.

Experiment 2

An experiment of the viscosity of the flush solution and the injection resistance value were conducted.

As the flush agent of the experiment, those of the examples 3, 4, 6, 7, 9, and 10 and those of the comparison examples 1, 4, and 5 were used. After the flush agents were filled in syringes having a volume of 20 mL, the syringes were connected to guiding catheters of 5Fr and 6Fr. In a state where the in-vivo insertion probe for image diagnosis and the guide wire are inserted into the guiding catheters, the flush agents were pressed out of the syringes by using AUTOGRAPH (produced by Shimazu Corporation). In the measurement of the injection resistance value, a maximum value of forces applied to the plunger of each syringe at the time when each flush agent was pressed out of each syringe was set as the injection resistance value in the examples and the comparison examples. The press-out speed of each flush agent was set to 100 mL/minute. The results are as shown in table 2.

TABLE 2

| Flush solution | Viscosity (mPa·s) | Injection resistance(N) Guiding catheter: 6Fr | Injection resistance(N) Guiding catheter: 5Fr |
| --- | --- | --- | --- |
| Example 3 | 1.1 | 10.4 | 40.7 |
| Example 4 | 1.0 | 9.2 | 39.2 |
| Example 6 | 1.0 | 10.1 | 37.925 |
| Example 7 | 1.4 | 15.4 | 47.725 |
| Example 9 | 1.0 | 10.0 | 55.7 |
| Example 10 | 1.1 | 10.1 | 53.9 |
| Comparison example 1 | 1.0 | 9.25 | 38.3 |
| Comparison example 4 | 4.8 | 31.25 | 147.75 |
| Comparison example 5 | 13.3 | 49.975 | 224.875 |

As shown in table 2, it was found that there was an increase in the injection resistance value in dependence on the viscosity when the guiding catheters of 6Fr and 5Fr were used. It was also found that the injection resistance value at the time when the guiding catheter of 5Fr was used was not less than four times as high as the injection resistance value at the time when the guiding catheter of 6Fr was used. The injection resistance values in the comparison examples 4 and 5 were very high when the guiding catheter of 5Fr was used. These results indicate that when the injection resistance value becomes excessively high, there is a possibility that the flush agent cannot be injected at a constant speed. As a result, in the experiment 1, it was judged that the flush solutions having high viscosities did not allow good image diagnostic performance to be obtained in the use of the guiding catheter of 5Fr, as their high viscosities.

Experiment 3

The image diagnosis of the flush solutions of the example 7 and the comparison examples 4 and 6 were checked by using an animal. After the guiding catheters of 6Fr and 5Fr were inserted respectively into a blood vessel of a pig, a prepared guide wire (outer diameter: 0.35 mm) was inserted into the catheter. An OFDI catheter was also inserted into the catheter. Each flush solution was injected into the blood vessel through the catheter. Of the obtained intravascular images, those allowing the inner wall of the blood vessel to be seen with eyes were defined as CLEAR FRAME. CLEAR FRAME time periods were calculated from the obtained intravascular images. FIGS. 9 and 10 show the results.

The results were that the CLEAR FRAME time period obtained in the example 7 of the present invention was longer than that obtained in the comparison example 4 and was equal to or longer than that obtained in the comparison example 6. The CLEAR FRAME time period obtained when the guiding catheter of 5Fr was used was equal to that obtained when the guiding catheter of 6Fr was used. The results of the experiment indicate that although the flush solution of the example had a low viscosity, it allowed image diagnostic performance to be obtained equivalently to a flush solution having a high viscosity. The results of the experiment also indicate that although the guiding catheter having a small inner diameter is used, the flush solution of the example allowed good image diagnostic performance to be obtained.

Description is made below on in-vivo intravascular blood replacing liquids of reference examples which can be used, although the viscosities thereof are higher than 2 mPa·s.

Reference Example 1

By adding 15 g of polyvinylpyrrolidone (produced by Sigma-Aldrich Corporation) having a molecular weight of 10,000 to 50 g of RO water and dissolving the polyvinylpyrrolidone in the RO water, the in-vivo intravascular blood replacing liquid (reference example 1) of the present invention was formed. The viscosity of the in-vivo intravascular blood replacing liquid of the reference example 1 was 7.5 mPa·s.

Reference Example 2

By adding 20 g of the polyvinylpyrrolidone produced by Sigma-Aldrich Corporation) having the molecular weight of 10,000 to 50 g of the RO water and dissolving the polyvinylpyrrolidone in the RO water, the in-vivo intravascular blood replacing liquid (reference example 2) of the present invention was formed. The viscosity of the in-vivo intravascular blood replacing liquid of the reference example 2 was 12.9 mPa·s.

Reference Example 3

By adding 5 g of the polyvinylpyrrolidone (produced by Sigma-Aldrich Corporation) having a molecular weight of 40,000 to 50 g of the RO water and dissolving the polyvinylpyrrolidone in the RO water, the in-vivo intravascular blood replacing liquid (reference example 3) of the present invention was formed. The viscosity of the in-vivo intravascular blood replacing liquid of the reference example 3 was 7.7 mPa·s.

Reference Example 4

By adding 7.5 g of the polyvinylpyrrolidone (produced by Sigma-Aldrich Corporation) having the molecular weight of 40,000 to 50 g of the RO water and dissolving the polyvinylpyrrolidone in the RO water, the in-vivo intravascular blood replacing liquid (reference example 4) of the present invention was formed. The viscosity of the in-vivo intravascular blood replacing liquid of the reference example 4 was 15.1 mPa·s.

Reference Example 5

1,000 mL of water was added to five phosphate buffered saline tablets (produced by Sigma-Aldrich Corporation) to prepare a phosphate buffer solution (PBS). The PBS was added to 25 g of polyvinylpyrrolidone (produced by Sigma-Aldrich Corporation) having a molecular weight of 40,000 to dissolve the latter in the former. The PBS was further added to the solution to set the volume thereof to 250 mL. In this manner, the in-vivo intravascular blood replacing liquid (reference example 5) was formed. The viscosity of the in-vivo intravascular blood replacing liquid of the reference example 5 was 6.2 mPa·s.

Comparison Example 7

As the in-vivo intravascular blood replacing liquid, the RO water was used. The viscosity of the in-vivo intravascular blood replacing liquid of the comparison example 7 was 1.0 mPa·s.

Comparison Example 8

As the in-vivo intravascular blood replacing liquid, the low molecular weight dextran (product name: "Otsuka Dextran L injection" produced by Otsuka Pharmaceutical Factory Co., Ltd) having the average molecular weight of 40,000 was used. The viscosity of the in-vivo intravascular blood replacing liquid of the comparison example 8 was 4.8 mPa·s.

Comparison Example 9

As the in-vivo intravascular blood replacing liquid, a non-ionic contrast agent (Omnipaque (registered trademark) 240 produced by Daiichi Sankyo Company, Ltd) was used. The viscosity of the in-vivo intravascular blood replacing liquid of the comparison example 9 was 6.4 mPa·s.

Comparison Example 10

As the in-vivo intravascular blood replacing liquid, the non-ionic contrast agent (Omnipaque (registered trademark) 300) was used. The viscosity of the in-vivo intravascular blood replacing liquid of the comparison example 10 was 13.3 mPa·s.

Experiment 4

The image diagnostic performance of the in-vivo intravascular blood replacing liquids of the reference examples 1 and 3 and the comparison examples 7, 8, and 9 was evaluated by using model blood.

Black pigment was used as the model blood. Image diagnostic performance was evaluated by analyzing images when each of the in-vivo intravascular blood replacing liquids was injected into the blood vessel and by using the number of the clear frames as the index.

The results were as shown below.
The number of the clear frames of the reference example 1: 124
The number of the clear frames of the reference example 3: 120
The number of the clear frames of the comparison example 7: 38
The number of the clear frames of the comparison example 8: 106
The number of the clear frames of the comparison example 9: 114

The in-vivo intravascular blood replacing liquids other than that of comparison example 7 allowed the number of the clear frames to be larger than that of the in-vivo intravascular blood replacing liquid (only RO water was used) of the comparison example 7. The in-vivo intravascular blood replacing liquid of the comparison example 8 (dextran was used) and that of the comparison example 9 (contrast agent was used) were almost equal to each other in the n umber of the clear frames. The in-vivo intravascular blood replacing liquids of the reference examples 1 and 3 allowed the number of the clear frames to be larger than those of the in-vivo intravascular blood replacing liquids of the comparison examples. Thus it was found that the blood replacing liquids of the reference examples 1 and 3 were useful in performing the image diagnosis.

Experiment 5

By using the in-vivo intravascular blood replacing liquids of the reference examples 1 through 3 and the comparison examples 9 and 10, image diagnostic performance was conducted as with the experiment 4. The results were as shown below.

The number of the clear frames of the reference example 1: 124
The number of the clear frames of the reference example 2: 149
The number of the clear frames of the reference example 3: 120
The number of the clear frames of the comparison example 9: 113
The number of the clear frames of the comparison example 10: 122

As the above results indicate, it was found that the number of the clear frames increases with an increase in the viscosity of the in-vivo intravascular blood replacing liquid both in the reference examples and the comparison examples. It was also found that in the in-vivo intravascular blood replacing liquids whose viscosities were almost equal to each other (for example, reference example 2 and comparison example 10), those of the examples allowed the number of the clear frames to be larger than those of the comparison examples and are thus effective.

Experiment 6

Intravascular image diagnosis was conducted on the flush solution of the reference example 5 and that of the comparison example 9 by using a pig. The results were as shown below.

The number of the clear frames of the reference example 5: 100
The number of the clear frames of the comparison example 9: 93

It was also found that the in-vivo intravascular blood replacing liquid of the reference example allowed the number of the clear frames to be larger than that of the in-vivo intra vascular blood replacing liquid of the comparison example and is thus effective.

INDUSTRIAL APPLICABILITY

The in-vivo intravascular blood replacing liquid of the present invention is as described below.
(1) In making an in-vivo intravascular inspection, an in-vivo intravascular blood replacing liquid is injected into a blood vessel to replace blood at an in-vivo intravascular portion to be inspected therewith. The blood replacing liquid comprises an aqueous medium unharmful for a living body and a gelling property imparting substance, unharmful for the living body, which is added to the aqueous medium to impart a gelling property to the blood replacing liquid. The blood replacing liquid has a viscosity of not more than 3 mPa·s when the blood replacing liquid is injected into the blood vessel.

The in-vivo intravascular blood replacing liquid (so-called flush solution) of the present invention has the viscosity of not more than 3 mPa·s when it is injected into the blood vessel. Therefore the resistance to the injection of the blood replacing liquid into the blood vessel is low. Thus the blood replacing liquid can be easily injected into the blood vessel. After the blood replacing liquid is injected into the blood vessel, it displays a sufficient blood pressing performance owing to the gelling property imparting substance contained therein and stays in the blood vessel for a certain period of time. Thus by using the in-vivo insertion probe for image diagnosis, it is possible to obtain the information for image diagnosis without being adversely affected by the blood.

The embodiment of the in-vivo intravascular blood replacing liquid may be as described below.

(2) An in-vivo intravascular blood replacing liquid according to the above (1), wherein said aqueous medium is sterile water, saline or a buffer solution.

(3) An in-vivo intravascular blood replacing liquid, according to the above (1) or (2), wherein said blood replacing liquid has a viscosity of not more than 3 mPa·s at not more than 30 degrees C. and displays a gelling property at not less than 25 degrees C.

(4) An in-vivo intravascular blood replacing liquid according to any one of the above (1) through (3), wherein said gelling property imparting substance is a mucoperiosteum, a polysaccharide thickener, or a compound having a phosphate group, a carboxylic acid group or a sulfate group; and said gelling property imparting substance includes glycyrrhizin acid, hyaluronic acid, chondroitin sulfate, alginic acid, ammonium sulfate, dextran sulfate, glucuronic acid, or salts or derivatives thereof.

(5) An in-vivo intravascular blood replacing liquid according to any one of the above (1) through (3), wherein said gelling property imparting substance is prepared by mixing not less than two kinds of compounds with each other; and said compounds gelate by chemical or physical interactions such as ionic bonds, hydrogen bonds or Van der Wools forces.

(6) An in-vivo intravascular blood replacing liquid according to the above (5), wherein said gelling property imparting substance is mixtures of glycyrrhizin acids and basic amino acids or derivatives thereof, mixtures of chitin or chitosan or derivatives thereof and hyarulonic acid or derivatives thereof, or mixtures of chondroitin sulfate or derivatives thereof and basic compounds.

(7) An in-vivo intravascular blood replacing liquid, according to any one of the above (1) through (6), which contains hydrophilic polymer as a viscosity modifier thereof.

(8) An in-vivo intravascular blood replacing liquid according to the above (7), wherein said viscosity modifier is at least one selected from the group consisting of gelatin, methylcellulose, polyethylene glycol, polyvinylpyrrolidone, ficoll, polyvinyl alcohol, styrene-maleic anhydride alternating copolymers, divinyl ether-maleic anhydride alternating copolymers, polyvinyl methyl ether, polyvinyl methyl oxazoline, poly ethyl oxazoline, poly hydroxypropyl oxazoline, poly hydroxypropyl methacrylamide, polymethacrylamide, polydimethylacrylamide, poly hydroxypropyl methacrylate, polyhydroxyethyl acrylate, hydroxymethyl cellulose, hydroxyethyl cellulose, polyaspartamide, and synthetic polyamino acid.

(9) An in-vivo intravascular blood replacing liquid formulation comprising a medical container and an in-vivo intravascular blood replacing liquid, according to any one of the above (1) through (8), which is contained therein.

Therefore it is very easy to perform the preparation operation of administering the in-vivo intravascular blood replacing liquid into an intravascular portion to be diagnosed.

The prefilled syringe of the present invention is as described below.

(10) A prefilled syringe comprising an outer cylinder, a gasket accommodated inside said outer cylinder, a sealing part for sealing a front end portion of said outer cylinder, and an in-vivo intravascular blood replacing liquid, according to any one of the above (1) through (8), which is filled inside said outer cylinder.

Therefore it is very easy to perform the preparation operation of administering the in-vivo intravascular blood replacing liquid into an intravascular portion to be diagnosed.

The embodiment of the prefilled syringe may be as described below.

(11) A prefilled syringe, according to the above (10), which is subjected to heat sterilization with said intravascular blood replacing liquid being filled therein.

The in-vivo intravascular blood replacing liquid formulation of the present invention comprises the medical container and the intravascular blood. replacing liquid filled therein.

The in-vivo intravascular blood replacing liquid is as described be

(12) In making the in-vivo intravascular inspection, the in-vivo intravascular blood replacing liquid of the present invention is injected into the blood vessel to replace blood at the in-vivo intravascular portion to be inspected therewith, The blood replacing liquid is a transparent aqueous liquid consisting of the aqueous medium unharmful for the living body and the hydrophilic polymer added to the aqueous medium to enhance the viscosity of the blood replacing liquid.

The in-vivo intravascular blood replacing liquid of the present invention has a high viscosity owing to the hydrophilic polymer contained therein. Thus when the blood replacing liquid is injected into the blood vessel, it displays a sufficient blood pressing performance. Further because the blood replacing liquid flows inside the blood vessel for a certain period of time, it is possible to obtain the information for image diagnosis without being adversely affected by the blood by using the in-vivo insertion probe for image diagnosis.

The embodiment of the in-vivo intravascular blood replacing liquid may be as described below.

(13) An in-vivo intravascular blood replacing liquid, according to the above (12), wherein said aqueous medium is sterile water, saline or a buffer solution.

(14) An in-vivo intravascular blood replacing liquid, according to the above (12) or (13), wherein said hydrophilic polymer does not have blood glucose level increasing property after in vivo administration.

(15) An in-vivo intravascular blood replacing liquid, according to any one of the above (12) through (14), wherein said hydrophilic polymer is polyethylene glycol, ficoll polyvinyl alcohol, styrene-maleic anhydride alternating copolymers, divinyl ether-maleic anhydride alternating copolymers, polyvinylpyrrolidone, polyvinyl methyl ether, polyvinyl methyl oxazoline, poly ethyl oxazoline, poly hydroxypropyl oxazoline, poly hydroxypropyl methacrylamide, polymethacrylamide, polydimethylacrylamide, poly hydroxypropyl methacrylate, polyhydroxyethyl acrylate, hydroxymethyl cellulose, hydroxyethyl cellulose, polyaspartamide, or synthetic polyamino acid.

(16) An in-vivo intravascular blood replacing liquid, according to the above (12) through (15), wherein said blood replacing liquid has a viscosity of 2 to 100 mPa·s.

(17) An in-vivo intravascular blood replacing liquid, according to the above (12), wherein said hydrophilic polymer is polyvinylpyrrolidone.

(18) An in-vivo intravascular blood replacing liquid, according to the above (12) through (17), wherein said hydrophilic polymer has a molecular weight of 200 to 1000000.

The in-vivo intravascular blood replacing liquid formulation of the present invention is as described below.

(19) An in-vivo intravascular blood replacing liquid formulation comprising a medical container and an intravascular blood replacing liquid, according to any one of the above (12) through (18), which is contained therein.

Therefore it is very easy to perform a preparation operation of administering the in-vivo intravascular blood replacing liquid into an intravascular portion to be diagnosed.

The prefilled syringe of the present invention is as described below.

(20) A prefilled syringe comprising an outer cylinder, a gasket slidably accommodated inside said outer cylinder, a sealing part for sealing a front end portion of said outer cylinder, and an in-vivo intravascular blood replacing liquid, according to any one of the above (12) through (18), which is filled inside said outer cylinder.

Therefore it is very easy to perform the preparation operation of administering the in-vivo intravascular blood replacing liquid into an intravascular portion to be diagnosed.

The embodiment of the prefilled syringe may be as described below

(21) A prefilled syringe, according to the above (20), which is subjected to heat sterilization with said intravascular blood replacing liquid being filled therein.

The invention claimed is:

1. An in-vivo intravascular blood replacing liquid comprising:
    an aqueous medium unharmful for a living body;
    a gelling property imparting substance, unharmful for said living body, which is added to said aqueous medium to impart a gelling property to said blood replacing liquid in an in-vivo intravascular inspection;
    said blood replacing liquid having a viscosity of not more than 3 mPa·s when said blood replacing liquid is injected into said blood vessel; and
    said gelling property imparting substance being mixtures of glycyrrhizin acids and thiamine chloride hydrochloride.

2. The in-vivo intravascular blood replacing liquid according to claim 1, wherein said aqueous medium is sterile water, saline, or a buffer solution.

3. The in-vivo intravascular blood replacing liquid, according to claim 1, wherein said blood replacing liquid has a viscosity of not more than 3 mPa·s at not more than 30 degrees C. and displays a gelling property at not less than 25 degrees C.

4. The in-vivo intravascular blood replacing liquid, according to claim 1, which contains a hydrophilic polymer as a viscosity modifier of the in-vivo intravascular blood replacing liquid.

5. The in-vivo intravascular blood replacing liquid according to claim 4, wherein said viscosity modifier is at least one selected from the group consisting of gelatin, methylcellulose, polyethylene glycol, polyvinylpyrrolidone, ficoll, polyvinyl alcohol, styrene-maleic anhydride alternating copolymers, divinyl ether-maleic anhydride alternating copolymers, polyvinyl methyl ether, polyvinyl methyl oxazoline, poly ethyl oxazoline, poly hydroxypropyl oxazoline, poly hydroxypropyl methacrylamide, polymethacrylamide, polydimethylacrylamide, poly hydroxypropyl methacrylate, polyhydroxyethyl acrylate, hydroxymethyl cellulose, hydroxyethyl cellulose, polyaspartamide, and synthetic polyamino acid.

6. An in-vivo intravascular blood replacing liquid formulation comprising a medical container and an in-vivo intravascular blood replacing liquid is contained therein, wherein said blood replacing liquid comprises an aqueous medium unharmful for a living body and a gelling property imparting substance comprising glycyrrhizin acids and thiamine chloride hydrochloride, unharmful for said living body, which is added to said aqueous medium to impart a gelling property to said blood replacing liquid; and said blood replacing liquid has a viscosity of not more than 3 mPa·s when said blood replacing liquid is injected into said blood vessel.

7. A prefilled syringe comprising an outer cylinder, a gasket accommodated inside said outer cylinder, a sealing part for sealing a front end portion of said outer cylinder, and an in-vivo intravascular blood replacing liquid is filled inside said outer cylinder,
    wherein blood replacing liquid comprises an aqueous medium unharmful for a living body and a gelling property imparting substance comprising glycyrrhizin acids and thiamine chloride hydrochloride, unharmful for said living body, which is added to said aqueous medium to impart a gelling property to said blood replacing liquid; and said blood replacing liquid has a viscosity of not more than 3 mPa·s when said blood replacing liquid is injected into said blood vessel.

8. A prefilled syringe, according to claim 7, which is subjected to heat sterilization with said intravascular blood replacing liquid being filled therein.

9. An in-vivo intravascular blood replacing liquid comprising:
    an aqueous medium unharmful for a living body;
    a gelling property imparting substance, unharmful for said living body, which is added to said aqueous medium to impart a gelling property to said blood replacing liquid in an in-vivo intravascular inspection;
    said blood replacing liquid having a viscosity of not more than 3 mPa·s when said blood replacing liquid is injected into said blood vessel; and
    said gelling property imparting substance being mixtures consisting of glycyrrhizin acids and thiamine chloride hydrochloride.

10. The in-vivo intravascular blood replacing liquid according to claim 9, wherein said aqueous medium is sterile water, saline, or a buffer solution.

11. The in-vivo intravascular blood replacing liquid, according to claim 9, wherein said blood replacing liquid has a viscosity of not more than 3 mPa·s at not more than 30 degrees C. and displays a gelling property at not less than 25 degrees C.

12. The in-vivo intravascular blood replacing liquid, according to claim 9, which contains a hydrophilic polymer as a viscosity modifier of the in-vivo intravascular blood replacing liquid.

13. The in-vivo intravascular blood replacing liquid according to claim 12, wherein said viscosity modifier is at least one selected from the group consisting of gelatin, methylcellulose, polyethylene glycol, polyvinylpyrrolidone, ficoll, polyvinyl alcohol, styrene-maleic anhydride alternating copolymers, divinyl ether-maleic anhydride alternating copolymers, polyvinyl methyl ether, polyvinyl methyl oxazoline, poly ethyl oxazoline, poly hydroxypropyl oxazoline, poly hydroxypropyl methacrylamide, polymethacrylamide, polydimethylacrylamide, poly hydroxypropyl methacrylate, polyhydroxyethyl acrylate, hydroxymethyl cellulose, hydroxyethyl cellulose, polyaspartamide, and synthetic polyamino acid.

* * * * *